(12) United States Patent
Gain et al.

(10) Patent No.: US 10,188,097 B2
(45) Date of Patent: Jan. 29, 2019

(54) MEDICAL DEVICE INTENDED FOR THE LONG-TERM STORAGE OF A CORNEA, OR FOR EX VIVO EXPERIMENTATION ON A HUMAN OR ANIMAL CORNEA

(71) Applicants: Universite Jean Monnet, Saint Etienne (FR); Ecole Nationale d'Ingenieurs de Saint-Etienne, Saint Etienne (FR); Etablissement Francais du Sang, La Plaine Saint Denis (FR)

(72) Inventors: Philippe Gain, Lyons (FR); Gilles Thuret, Saint Just Saint Rambert (FR); Sophie Laverne-Acquart, Saint-Chamond (FR); Sébastien Soubaigne, Perigneux (FR)

(73) Assignees: UNIVERSITE JEAN MONNET, Saint Etienne (FR); ECOLE NATIONALE D'INGENIEURS DE SAINT-ETIENNE, Saint Etienne (FR); ETABLISSEMENT FRANCAIS DU SANG, La Plaine Saint Denis (FR)

( * ) Notice: Subject to any disclaimer, the term of this patent is extended or adjusted under 35 U.S.C. 154(b) by 505 days.

(21) Appl. No.: 14/776,618

(22) PCT Filed: Mar. 14, 2013

(86) PCT No.: PCT/FR2013/050530
§ 371 (c)(1),
(2) Date: Sep. 14, 2015

(87) PCT Pub. No.: WO2014/140434
PCT Pub. Date: Sep. 18, 2014

(65) Prior Publication Data
US 2016/0029618 A1 Feb. 4, 2016

(51) Int. Cl.
A01N 1/02 (2006.01)

(52) U.S. Cl.
CPC .......... *A01N 1/0247* (2013.01); *A01N 1/0263* (2013.01)

(58) Field of Classification Search
CPC .... A01N 1/0247; A01N 1/0263; B01D 63/08; B01D 61/18; C12M 1/12; G01N 13/00; G01N 33/15; G01N 2013/003
See application file for complete search history.

(56) References Cited

U.S. PATENT DOCUMENTS

| 4,205,747 A | * | 6/1980 | Gilliam | ............... A45C 11/005 206/5.1 |
| 5,030,575 A | | 7/1991 | Stofac | |

(Continued)

FOREIGN PATENT DOCUMENTS

| EP | 0 262 766 A1 | 4/1988 |
| FR | 2 944 185 A1 | 10/2010 |
| FR | 2 986 133 A1 | 8/2013 |

OTHER PUBLICATIONS

Thiel, M.A., et al., "A Simple Corneal Perfusion Chamber for Drug Penetration and Toxicity Studies," *British Journal of Ophthalmology* 85:450-453, Jan. 2001.

*Primary Examiner* — William H. Beisner
*Assistant Examiner* — Danielle B Henkel
(74) *Attorney, Agent, or Firm* — Seed Intellectual Property Law Group LLP

(57) ABSTRACT

A device for the storage of a corneal specimen has means for the reception and entrapment of a corneal specimen, connected to the means for the creation of a pressure gradient with overpressure on the endothelial side and to the preservation medium circulation means in the layouts that present the means for the reception and entrapment of the cornea specimen. The means for the reception and entrapment of the corneal specimen entrap the sclera ciliary zone surrounding the cornea in an airtight manner to delimit a separate (Continued)

endothelial chamber and epithelial chamber in which the preservation medium can circulate with an overpressure in the endothelial chamber; The intermediate component and the endothelial lid comprise inlet and outlet orifices for the preservation medium which are connected to the means for the circulation of the preservation medium and the creation of a pressure gradient between the endothelial chamber and the epithelial chamber with overpressure in the endothelial chamber.

14 Claims, 7 Drawing Sheets

(56) References Cited

U.S. PATENT DOCUMENTS

| | | | |
|---|---|---|---|
| 5,591,636 A * | 1/1997 | Grass | B01D 61/18 |
| | | | 324/450 |
| 5,789,240 A | 8/1998 | Abdulrazik | |
| 6,773,916 B1 * | 8/2004 | Thiel | C07K 16/28 |
| | | | 435/326 |
| 7,449,307 B2 * | 11/2008 | Cima | B01L 3/5085 |
| | | | 424/449 |
| 2008/0294149 A1 | 11/2008 | Krolman | |

* cited by examiner

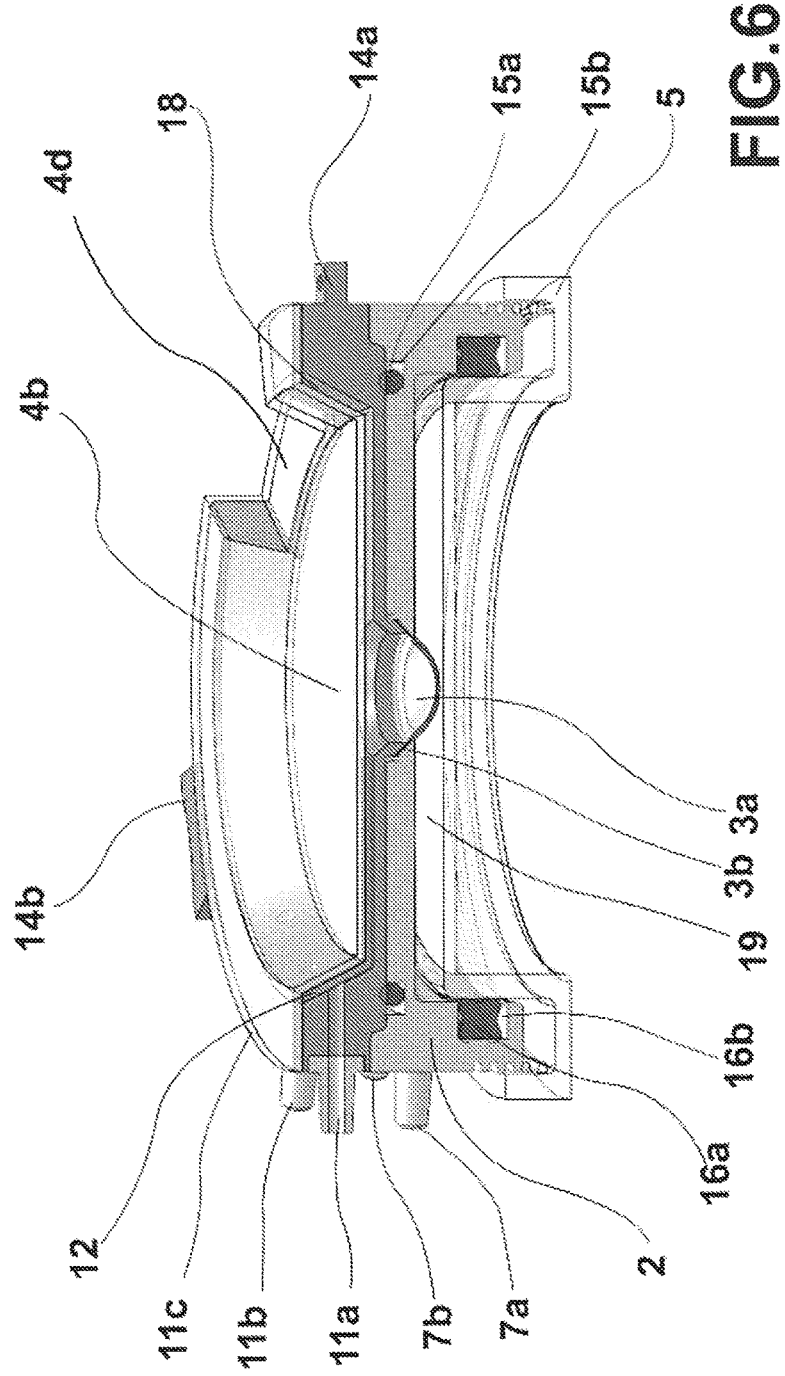

MEDICAL DEVICE INTENDED FOR THE LONG-TERM STORAGE OF A CORNEA, OR FOR EX VIVO EXPERIMENTATION ON A HUMAN OR ANIMAL CORNEA

BACKGROUND

Technical Field

The invention relates to the technical sector of medical devices intended for the long-term storage of a cornea, in particular for grafting, or for ex vivo experimentation on human or animal cornea.

Description of the Related Art

Depending on the state of the technique, cornea grafts are stored throughout the world mainly in two different manners: either at +4° C. for a short period (maximum 10 days) using a technique called cold storage, or according to a technique called organ culture at a temperature ranging from +31° C. to +37° C. Organ culture uses a nutrient medium derived from cell culture media that allows a long-term storage of up to five weeks. It is a sequential technique including an initial phase during which the cornea becomes oedematous (its thickness is multiplied by two, going from 500-600 μm to 1000-1200 μm) and folds over on its posterior face, and a second phase over 12 to 72 hours during which the graft is immersed in the same organ culture medium but with an added macromolecule (Dextran T500 or poloxamer 188) which diminishes the turgidity of the graft to reduce its thickness and decrease the posterior fold right before graft.

In both of these techniques the grafts are immersed either in simple glass or plastic bottles in which the cornea is free, or in boxes where the cornea is partially immobilized in a cage or basket (like a contact lens case). In both cases there is no circulation of the storage medium, nor maintenance of a pressure gradient on either side of the cornea.

However, in order to be stored in an optimal manner, the graft must be in conditions similar to those found in its physiological environment. The physiological parameters to be reproduced are specifically those of the anterior chamber of the eye, i.e., intra-ocular pressure of the order of 18 millimeters of mercury (mmHg) and a temperature of the order of 31 to 37° for a human eye for example, and the circulation of a cornea storage liquid both on the endothelial side (mimicking the permanent renewal of the aqueous humor) and on the epithelial side (mimicking the permanent circulation of tears). If these conditions are not reproduced, the cornea cells death is accelerated especially in the posterior fold zones and the corneal stroma becomes oedematous and there is a transient loss of its transparency.

U.S. Pat. No. 5,789,240 describes a cornea assembly device that simulates the anterior chamber of the eye. This device allows reproducing the intra-ocular pressure, temperature and intraocular liquid circulation parameters but it is solely intended for laboratory experimentation to carry out drug penetration tests. This device does not allow storing corneal grafts prior to cornea transplant in a patient. In particular, it does not allow the sterile circulation of preservation liquid on both sides of the cornea, i.e., both the epithelial and endothelial sides. It is not fully transparent to allow examining the cornea without opening the device. Therefore, the survival time of the cornea has to be short and is incompatible with using it for a cornea transplant.

French Patent No. 2944185 describes a "perfusion chamber" for corneas designed to be in a vertical position only, to mimic the flow of tears. This perfusion chamber is also intended for laboratory experiments, in particular preclinical toxicity studies but not for the storage of corneal grafts before transplant. It comprises an endothelial compartment designed to be filled with gel to keep the shape of the cornea but does not include any circulation of nutrient liquid on the endothelial side. It does not include a pressure gradient maintenance system on either side of the cornea. It is not transparent throughout.

The article from British Journal of Ophthalmology 2001; 85:450-3 "A simple corneal perfusion chamber for drug penetration and toxicity studies" presents a polycarbonate chamber developed to receive a human cornea, however it has only been tested with pig and cat cornea. It includes a closed circuit liquid circulation set into motion by a peristaltic pump. The 18 mmHg pressure gradient is maintained by gravity (bottle containing the perfusion liquid placed at a height). The corneal epithelium is in contact with the ear and the epithelial compartment is not airtight. It is not transparent throughout. This perfusion chamber is not intended for the storage of cornea specimens prior to transplant either.

Furthermore, none of the previous art devices allow flattening the cornea to allow LASER cutting of the corneal tissue or facilitating the observation of endothelial cells on a flat surface. In the current state of the art, the cornea are cut with a femtosecond LASER on specific supports which are not appropriate for the storage of grafts. In the prior state of the art, the grafts had to be extracted from their storage medium, manually placed on a specific support exposed to ambient air and then placed under the LASER cutting system. To flatten the cornea another device must be attached to the actual LASER and not to the corneal specimen support.

Finally, none of the prior art devices claims the possibility of performing a graft cell therapy.

Concerning the use of prior art devices for ex vivo experiments on the penetration of molecules and toxicity studies, none of them combines the following characteristics: allow a sterile storage of human or animal cornea on the long-term (several weeks), include a pressure gradient on the endothelial side, include the circulation of liquid on both sides of the cornea, being transparent throughout and having a cornea flattening device.

BRIEF SUMMARY

The objective the invention fixed itself is to rectify these disadvantages in a simple, safe, effective and rational manner.

The problem that the invention proposes to solve is to create a long-term human cornea storage device which allows:

sterile circulation of preservation liquid on both sides of the cornea, creating a pressure gradient between the two sides of the cornea with an overpressure on the endothelial side.

examination of cornea through and through, flattening of the corneal dome without opening the bioreaction, i.e., without threatening the sterility of the corneal specimen.

Therefore, the objective sought is to keep the ex vivo cornea in a quasi physiological condition in order to improve the storage of corneal grafts prior to transplant and also for performing basic and/or pre-clinical ex vivo experiments.

The device is of course not limited to the storage of the cornea or experiments on the cornea in the human species. It also allows experiments on corneas from any animal species with a different corneal diameter to that of humans. The geometry of the bioreaction (mainly the diameter of the central recess of the cornea), as well as the temperature, pressure and storage liquid composition conditions can be varied as desired depending on the animal species of the cornea to be stored.

To solve such a problem, we designed and developed a device for the storage of cornea which includes:
  means for the reception and entrapment of the cornea specimen, connected to means for putting the cornea under pressure that can be adjusted,
  means for the injection of a preservation liquid in the layout of the means for the reception and entrapment of the cornea,
  means for flattening the corneal dome,
  means for sampling the storage medium for microbiological and/or biochemical testing purposes, and
  means for the injection of substances into the bioreactor without having to open it.

According to the invention this device is remarkable in that the layouts that present the means for the reception and entrapment of the cornea immobilize the cornea by pinching the sclera ciliary zone surrounding it, which enables contact between the preservation liquid and the two faces of the cornea. Two spaces called the endothelial chamber and the epithelial chamber are thus delimited.

Advantageously the preservation liquid in the device according to the invention is at a temperature ranging between 1 and 40° C. covering the range of temperatures used for the storage of cornea throughout the world.

Advantageously and to enable inspection through and through of the condition of the cornea at any moment, the layouts of the means for the reception and entrapment of the cornea include through and through means for the inspection of the cornea based on the transparency of the parts of the bioreactor surrounding the cornea.

In a preferred form of embodiment of the invention, the device comprises three sections:
  a first section called intermediate component which serves for the reception and support of the corneal specimen and participates in its entrapment with the second section named endothelial lid. The intermediate component includes a central hole of the diameter of the cornea (variable according to the animal species). The edges of this hole are prolonged by a circular groove intended to receive the sclera. The corneal specimen is placed, epithelium down, on this hole and is maintained by its sclera ciliary zone which lays on this groove. At the edge of this rim there is a circular rim that prevents the cornea from moving sideways and coming out of the recess delimited in this manner. The cornea is thus automatically centered on the hole of the intermediate component.
  a second section named endothelial lid, intended to clip unto the upper face of the intermediate component. This endothelial lid may be itself formed of two joined parts which delimit a space called the endothelial chamber in which the preservation medium circulates in contact with the endothelial face of the cornea. The lower portion of this lid is pierced by a hole of the same diameter as that of the intermediate component. The edges of this hole have a circular edge intended to correspond to the groove of the intermediate component to flatten the sclera so as to make the contact tight at the level of the sclera and to properly separate the endothelial and epithelial chambers. The cornea is thus solidly entrapped between the intermediate component and the endothelial lid. The upper section of the endothelial lid is transparent in order to enable the observation of the cornea without having to open the endothelial chamber of the bioreactor.

The endothelial lid includes a large notch on the edge, intended to allow passing through the objective of an upright optical microscope, a specular microscope, an optical coherence tomograph (OCT), a LASER or any other instrument intended for the analysis of treatment of the cornea and which need to get as close to the cornea as possible.

A progressive blockage system using two slanted sliders (one on the endothelial lid and one on the intermediate component) between the endothelial lid and the intermediate component allows optimum flattening of the sclera ciliary zones irrespective of its thickness. These sliders are micro-crenelated on their surface, which increases the friction between them and prevents them being suddenly unblocked when the bioreactor is handled.
  a third section, named the epithelial lid, screws on the inferior face of the intermediate component for form an airtight compartment on the corneal epithelial side, thus forming an epithelial chamber. This lid can be adjusted to bring it closer to the epithelial side of the cornea, thus allowing a controlled flattening of the cornea. The flattening surface may be flat or curved. The epithelial lid may be in non-flattened position (not in contact with the epithelium) or in flattening position via a step-by-step or progressive adjustment device. The epithelial lid is also transparent to enable the examination of the cornea without opening the epithelial lid of the bioreactor. The lid may be removed during experimental use (and not during the storage of corneal specimens for transplantation), as during eye drop instillation and molecule penetration tests through the cornea for example. This opening of the epithelial lid does not perturb the maintenance of the overpressure in the endothelial chamber.

Joints of different types, mainly O- or Quad-rings, in biocompatible materials guarantee the tightness and sterility between these three sections.

Advantageously, the two transparent faces of the endothelial lid and the epithelial lid are aligned with the holes of the intermediate parts and the endothelial lid. They thus allow an obstacle-free passage of light through the cornea without having to open the bioreactor. This could be visible light to perform visual or instrumental tests of the cornea by an observer. Non-comprehensive list of examples: analysis of the transparency of the cornea (for example with the usual slit lamp of ophthalmologists), cell counts, in particular endothelial, study of buried interfaces of refractive surgery. This could also include ultraviolet radiation to perform collagen cross-linking of the corneal graft. Finally, it could also be a LASER beam for analysis (e.g., optical coherence tomography imaging), cell therapy (the LASER activating the biological processes within the cornea), or tissue therapy (the LASER cutting the cornea). Finally, other light wavelengths may also be used through the bioreactor.

Advantageously, the two faces of the endothelial lid and the epithelial lid are made in a low ultrasound reflection material to allow the ultrasonography analysis of the cornea (for example measuring the thickness before and after LASER cutting) without opening the bioreactor.

The endothelial chamber and the epithelial chamber comprise several orifices. There is a minimum, non-limiting, of at least three orifices in each compartment: a storage medium inlet orifice, a storage medium outlet orifice and an additional orifice called "technical" (for the removal or medium samples or the injection of substances). The endothelial lid also includes an orifice designed to receive a pressure sensor. The epithelial lid can also include one. The means for putting under pressure and for the control of the pressure take place through these orifices. The liquid inlet orifice in the endothelial continues inside the chamber through a trough that forces the fresh medium to pour as close as possible to the corneal endothelium.

The inlet/outlet orifices, present in both chambers, enable the preservation liquid to circulate and to be flushed out to optimize the storage of the cornea.

These orifices also allow varying the pressure within the compartments so as to always have an overpressure on the endothelial side. The latter may also be equal to the pressure that the cornea encounters physiologically on the endothelial side or any other pressure chosen. For example 12 to 20 mmHg for a human cornea. This overpressure may be obtained by controlling the volume injected in the endothelial chamber and the volume of liquid coming out.

For example, the preservation medium is contained in an overpressurized reservoir, in particular an elastomeric membrane, spring or pressurized gas infusion device. The pressure may also be generated by a peristaltic pump or another type of pump.

In an initial production example, the medium under pressure goes through a glass capillary type flow rate regulator, then through a micro-solenoid valve and is then injected into the endothelial chamber. The opening and closing of the micro-solenoid valve are controlled by an electronic controller according to a set point predetermined by the user (e.g., 18 mmHg) and adjusted according to the pressure measured by an electronic pressure sensor placed in the endothelial chamber. The liquid coming out of the endothelial chamber goes through a second flow rate regulator before going through the epithelial chamber and then pouring into a so-called "waste" reservoir that comes into contact with the atmospheric pressure through a filter that guarantees sterility.

In a second production example, the control of the pressure is passive: the pressurized liquid is injected into the endothelial chamber. It comes out and goes through the control valve referred to as "check valve" chosen to open at the selected pressure, the pressure in the endothelial is thus maintained at the level of the opening pressure of the valve as long as the medium is injected.

The two "technical" orifices (in the endothelial chamber and the epithelial chamber) also allow taking a sample of preservation liquid for microbiological testing (sterility test) or biochemical testing (modifications of the characteristics of the medium, especially of the pH), or to inject any product during the preservation phase, such as a dye (Trypan blue to test cell mortality) or a medicinal product, or a gene, without having to open any compartment or handle the cornea. This may enable carrying out a cell therapy of the graft via the injection of reagents in the endothelial chamber for example, to modify the biological behavior of the corneal cells (gene therapy for example).

Advantageously, in the device according to the invention, the intermediate component and the endothelial lid include the additional means for locking them to each other, which enable keeping the compartments in the joined position. These additional locking and unlocking means exists as biased sliding joints that allow a progressive compression of the two parts (endothelial cover and intermediate component) in order to block the cornea in an optimal manner via the progressive and controlled crushing of the scleral ciliary zone.

Such a device can remain closed for example between the removal of the cornea from the donor until the transplantation by the surgeon. It is only opened at the operating theater to release the cornea for surgery.

The other characteristics and advantages of the invention will become clear from the description below, including but not limited to, referring to the figures in the annexes.

BRIEF DESCRIPTION OF THE SEVERAL VIEWS OF THE DRAWINGS

For a better understanding of the invention, several diagrams are presented with invariable numbered parts irrespective of the diagram. The parts or elements from a production form which are found in an identical or similar manner in another form of production will be identified with the same number references for the sake of simplicity and will not be described again.

FIG. 6 shows a perspective and cross-sectional view of the assembled device with a corneal specimen in position.

DETAILED DESCRIPTION

Figure 1:
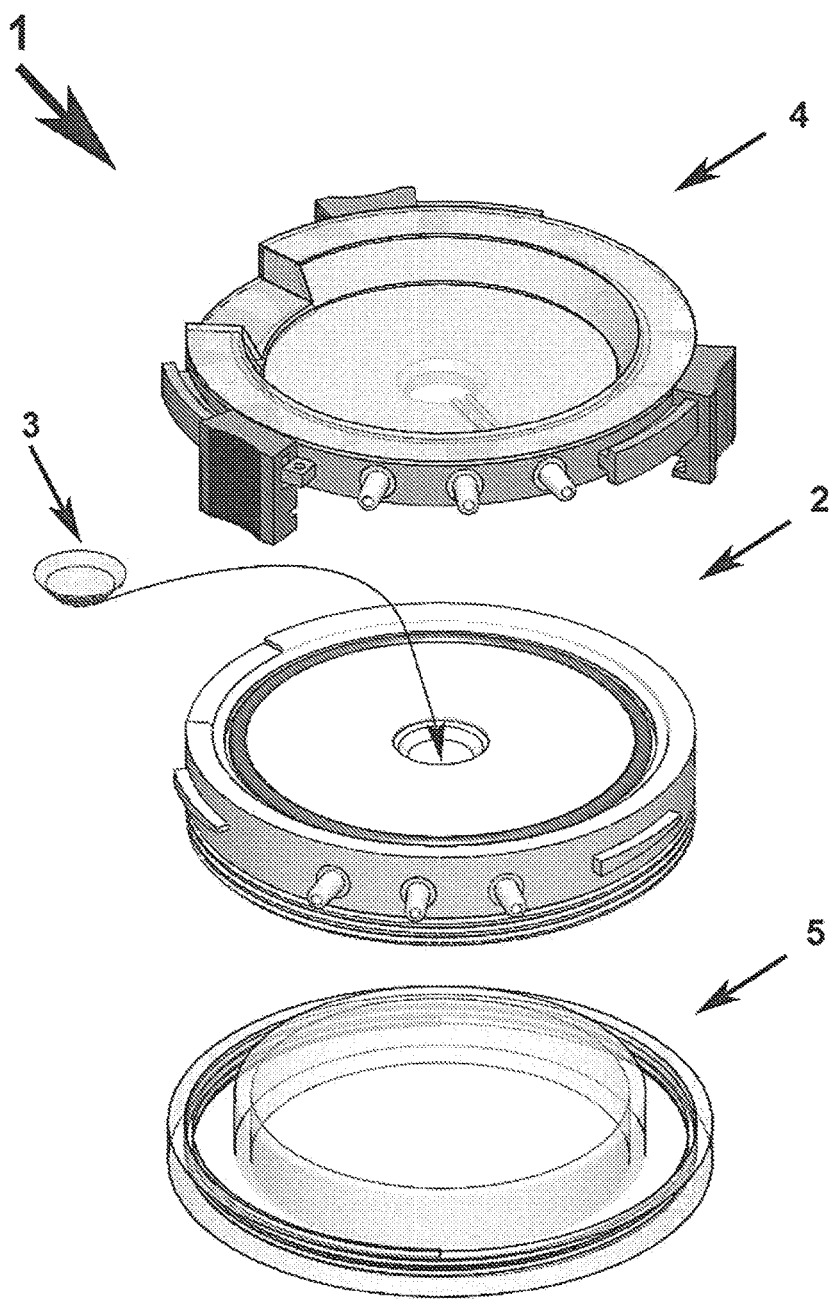
FIG. 1 is a perspective exploded view of the elements composing the device: endothelial lid, intermediate corneal specimen support component, epithelial lid with adjustable flattening.
Figure 7:
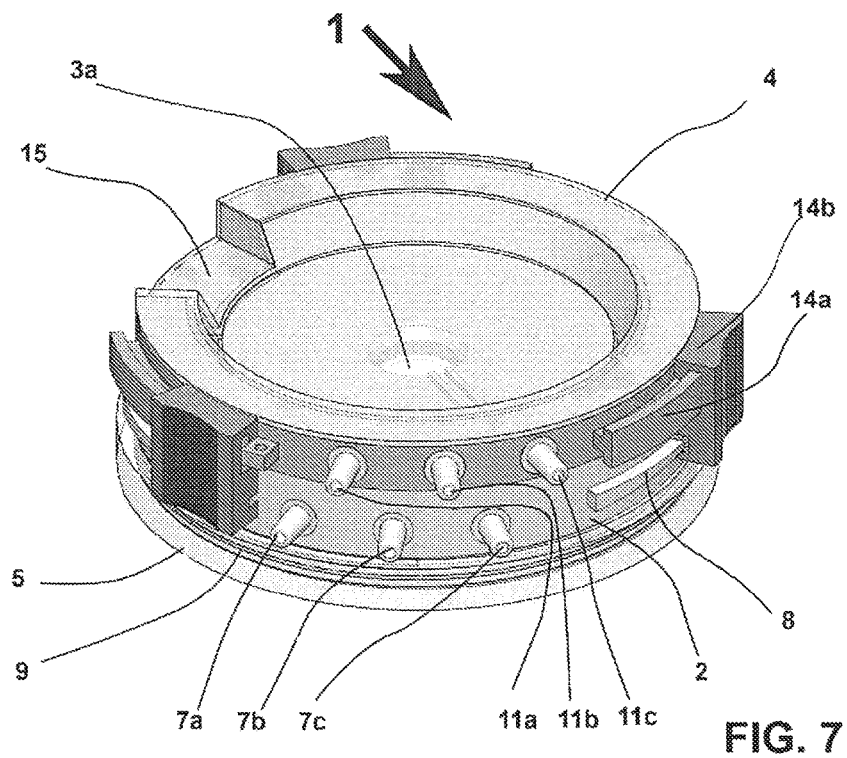
FIG. 7 shows a perspective and cross-sectional view of the assembled device with a corneal specimen in position.

Referring to FIGS. 1 and 7, the device is a bioreactor 1 comprising an intermediate corneal specimen support component 2, an upper component referred to as the endothelial lid 4 and a lower component named the epithelial lid 5.

Figure 2A:
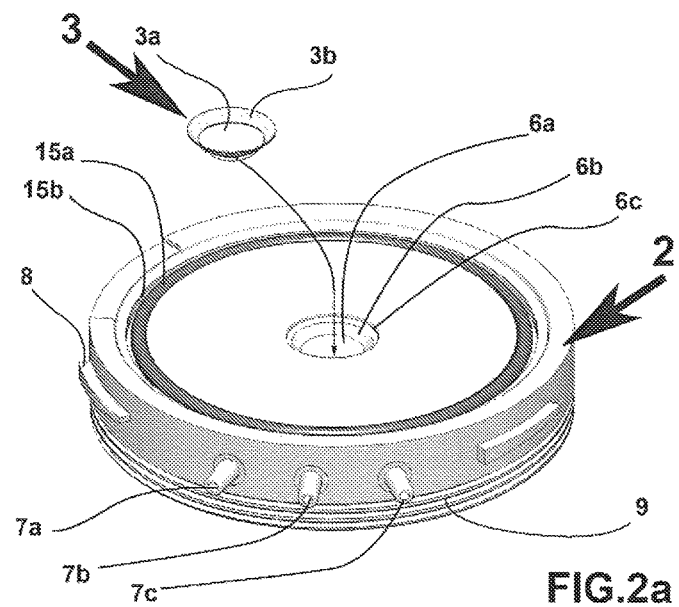
FIGS. 2a and 2b are upper and lower perspective views, respectively, of the intermediate corneal specimen support component.
Figure 2B:
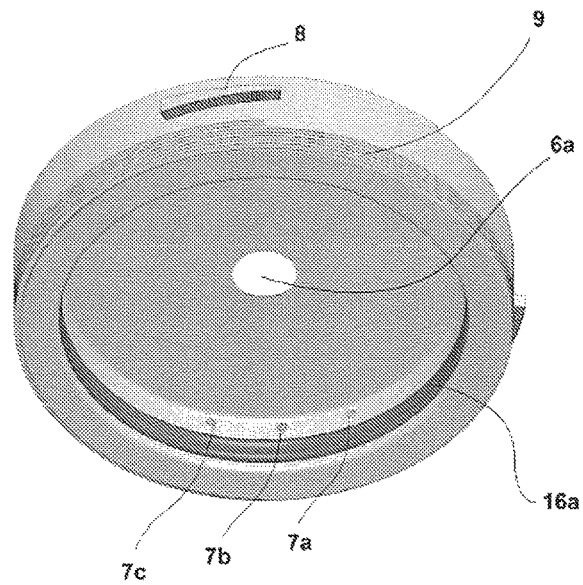

Referring to FIGS. 2a and 2b, the intermediate component 2 has a central hole 6a corresponding to the diameter of the cornea 3a, surrounded by a circumferential groove 6b and edge 6c forming a recess intended to receive the sclera central 3b. It also includes at least 3 orifices 7a, 7b, 7c allows the entrance or exit of the preservation medium or of any other substance of the epithelial side of the cornea 3a. The orifice 7a may be used for the injection of the medium, the second 7b for the outlet of the medium and the third 7c is a so-called technical orifice for the injection or withdrawal of medium or additional substance without having to interrupt the flow in the first two orifices. Preservation medium circulation tubes can be fitted on these orifices as well as plugs (standard stopping plugs or stopping plugs that can be perforated with a sterile needle, to remove samples or inject substances, for example). This intermediate component comprises additional locking means 8 with the endothelial lid 4. These means can be three sliding joints 8 placed at 120° on the circumference of the intermediate component 2 and designed to receive a locking system 14b. One of the faces of this sliding going is at an angle relative to horizontal and allows a progressive tightening of the endothelial lid 4 on the intermediate component. The tightening flattens the sclera ciliary zone 3b which creates an actual seal between the two components. The slanted plane of the sliding joint 8 is micro-crenated in order to increase the friction with the corresponding slanted plane on the locking system 14b. The increased friction prevents a sudden unlocking of the 2 components during handling of the bioreactor 1. The seal with the endothelial lid 4 is ensured by a ring joint 15a lodged in a circular groove 15b. As an example, this joint could be an O-ring 15b. The seal with the epithelial lid 5 is ensured by a ring joint 16a lodged in a circular groove 16b. As an example, this joint could be a Quad-ring 16b chosen for its good translation performance. The intermediate component also includes a system that allows adjusting the flattening of the cornea by the epithelial lid 5, for example using a screw thread 9 which thus allows an adjustable flattening.

Figure 3A:
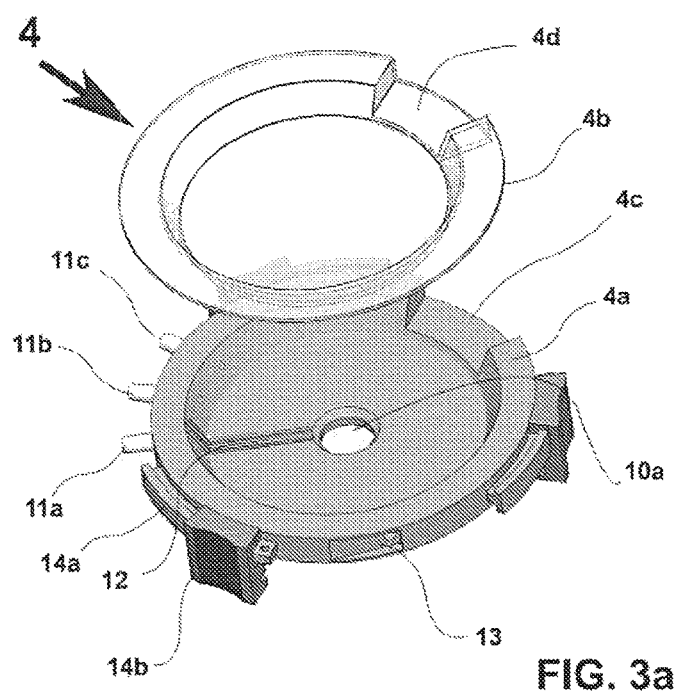
FIGS. 3a and 3b are upper and lower perspective views, respectively, of the assembly of the 2 parts composing the endothelial lid.
Figure 3B:
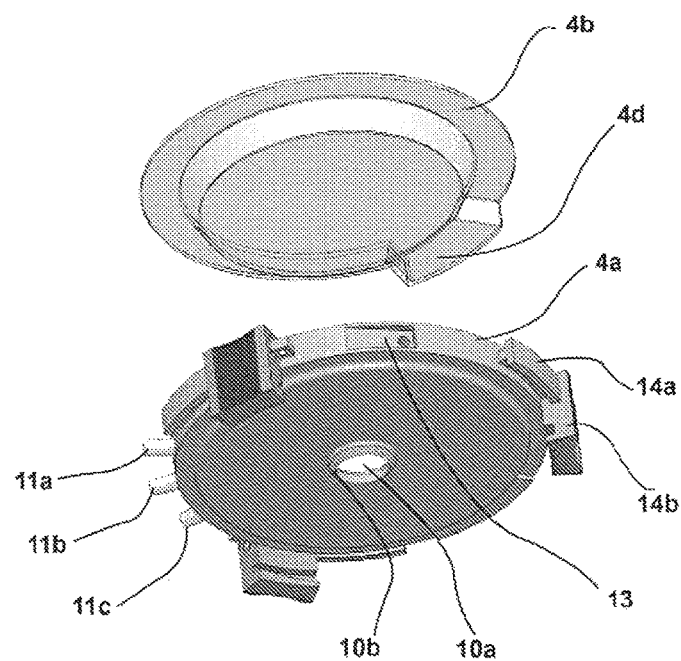

Referring to FIGS. 3a and 3b, the endothelial lid 4 is made in two sections. A first section 4a functioning as cylindrical container and a second section 4b functioning as a transparent lid. These two components are assembled in a water-tight manner, e.g., by gluing them, and delimit the endothelial chamber 18 on FIG. 6. The first component 4a includes a hole 10a in its bottom that allows the liquid to reach the cornea endothelium 3a. The edges 10b of this hole 10a protrude into the intermediate component 3, to correspond to the circumferential groove 6b so as to trap the cornea specimen while flattening the sclera 3b between the intermediate component 2 and the endothelial lid 4 thanks to the additional locking system 8, 14a, 14b. The holes of the intermediate component and the endothelial lid are coaxial. The side wall of the endothelial lid 4a has inlet 11a or outlet 11b orifices for the preservation medium, intended to be connected to the bioreactor pressure means 1 and a "technical" orifice 11c to take samples or inject preservation medium or any other substance, without having to interrupt the flow of the first two. These orifices can receive preservation medium circulation tubes or plugs (standard or pierceable). The preservation medium injection orifice 11a in the endothelial chamber emerges in a groove 12 which directs the fresh preservation medium directly unto the endothelial face of the cornea 3a. The side wall of the component 4a also includes an orifice 13 for the insertion of an electronic pressure micro-sensor. The endothelial lid comprises additional locking means 14a with the intermediate component 2. These means can be 3 rails 14a placed at 120° on the circumference of the endothelial lid 4 and designed to receive the locking system 14b. This system slides on the rail. It is described in detail in FIG. 5a and FIG. 5b. The endothelial lid 4 can lock tightly unto the intermediate component 2 to delimit a space called endothelial chamber 18 trapping the corneal specimen 3. The tightness is provided by O-rings 15a lodged in a groove 15b made in the intermediate component 2. The endothelial lid includes a large notch 4c and 4d on the edge, intended to allow passing through the objective of an upright optical microscope, a specular microscope, an optical coherence tomograph (OCT), a LASER or any other instrument intended for the analysis of treatment of the cornea and which need to get as close to the cornea as possible.

Figure 4:
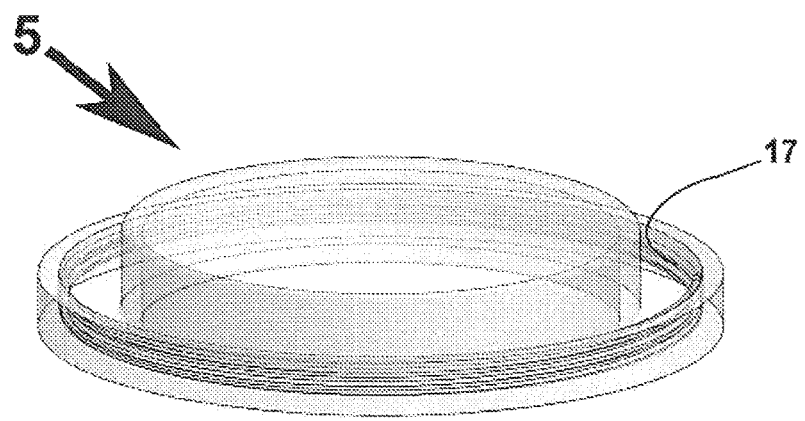
FIG. 4 is an upper perspective view of the epithelial lid.

Referring to FIG. 4, the epithelial lid 5 is transparent. It can lock tightly unto the intermediate component 2 to delimit a space called epithelial chamber (19 on FIG. 6). It includes a system that allows the adjustable flattening of the cornea 3 by pressing into the intermediate component. This system may be for example a screw thread 17 sliding into the additional screw thread 9 of the intermediate component thus allows an accurate and selectable flattening. The surface that comes into contact with the epithelial side of the cornea 3a can be flat as shown here or curved.

Figures 5A, 5B:
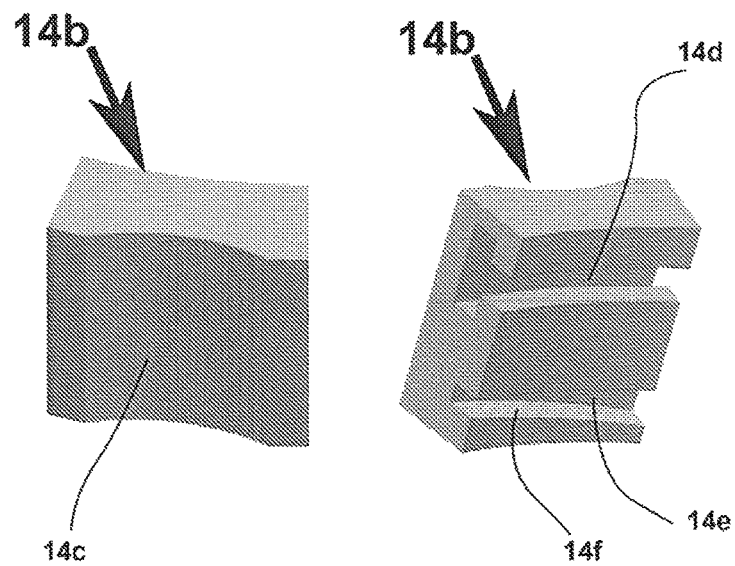
FIGS. 5a and 5b are front and back perspective views, respectively, of the additional closure system between the endothelial lid and the intermediate component.

Referring to FIGS. 5a and 5b, the additional closure system between the endothelial lid 4 and the intermediate component 2 is composed on the one hand of 3 rails 14a connected to the external side of component 4a of the endothelial lid on its circumference and positioned at 120°, and on the other hand 3 locking systems 14b which slide on the rails 14a. The upper portion of the locking system 14b includes a T groove 14d that can slide on the rail 14a with a complementary shape. The lower portion of the closure system 14b includes a groove 14e with biased edges 14f. This biased section 14 can come into contact with a rail 8 which is also made biased and connected to the intermediate component 2, so that the translation of the closure system 14b on the rail 14a encounters these 2 surfaces at an angle and provokes the progressive tightening of the endothelial lid 4 on the intermediate component 2. The tightening crushes the sclera ciliary zone 3b between the surfaces 6b and 10b at the edge of holes 6a and 10a of the intermediate component 2 and the endothelial lid 4, respectively. The tightening carried out on the sclera 3b fully immobilizes the corneal specimen 3 while preserving the integrity of the cornea 3a. The two biased sections of the rail 8 and of the locking system 14b are micro-crenellated to make them easier to block one against the other and prevent sudden unlocking. The external portion 14c of the locking system is also micro-crenellated to make it easier to grab between the fingers.

Referring to FIG. 6, the bioreactor 1 is completely transparent opposite the cornea 3 thanks to the transparent walls of the endothelial 4 and epithelial 5 lids, located opposite the two coaxial holes 6a and 10a of the intermediate components 2 and the endothelial lid 4, respectively. This transparency allows visible light to pass without obstacles (visual or instrumental controls of the cornea by an examiner), as well as ultraviolet light (e.g., cross-linking of corneal collagen), LASER beams intended for analysis purposes (e.g., optical coherence tomography imaging), cell therapy (activation of biological processes within the cornea), or tissue therapy (cutting the cornea) or of any other light wavelength. All of these operations may be performed at any moment and without having to open the bioreactor. The endothelial lid 4 delimits the endothelial chamber 18 once it has been closed over the intermediate component 2. The space between the intermediate component 2 and the epithelial lid 5 delimits the epithelial chamber 19.

In practice the use of the bioreactor 19 according to the invention, for cornea transplantation is divided in three stages: stage 1 removal from donor, stage 2 storage by the cornea bank followed by stage 3 transplantation in the operating theater.

During the stage 1 removal, the intermediate component 2 and the endothelial lid 4 are separated while the intermediate component 2 and the epithelial lid 5 are joined. The cornea specimen 3 is placed in the cavity formed by the edges 6b and 6c of the hole 6a of the intermediate component 2. The endothelial lid 4 is then clicked onto the intermediate component 2, thus trapping the cornea specimen 3 between two sections 2, 4 by crushing its scleral ciliary zone 3b. The cornea 3a then has its endothelial side exposed to the endothelial chamber 18 and its epithelial side exposed to the epithelial chamber 19. We then close the additional locking means by sliding the 3 locking systems 14b with the fingers along the rails 14a. The preservation medium circulation tubes are then connected to the orifices 7a, 7b and 11a, 11b of the intermediate component 2 and of the endothelial lid 4. In another production form, the tubes may previously fitted on the endothelial lid 4 and intermediate component 2. The technical orifices 7c and 11c remain closed with simple stopping plugs or stopping plugs that can be pierced. The tubes are connected to the preservation medium circulation and pressure gradient devices with an overpressure in the endothelial chamber (described in FIG. 8 and FIG. 9).

During stage 2, storage in a cornea bank, the bioreactor enables keeping the cornea cells viable, prevents cornea oedema, a source of tissue transparency loss, and limits posterior folds which are responsible for an excess mortality of corneal endothelial cells. The bioreactor may be used at any temperature between 1 and 40° C., depending on the preservation medium. The quality control tests on the cornea can be performed without opening the bioreactor as it has the advantage of being transparent through and through and composed of a material compatible with the use of ultrasounds. Furthermore, it is functional in any position (horizontal or vertical) and has a large notch in the endothelial lid 4 to facilitate the passage of measuring or treatment devices for the graft. The quality controls could include the following without being limited to them: evaluation of transparency (via the examination with an ophthalmologist slit lamp or any other transparency quantification device), thickness measurements (of the entire graft or of the cut graft), counting endothelial cells either by specular microscopy without preparation or by standard optical microscopy after prepping the graft (the reagents required for prepping the graft may be injected via the technical orifice 11c of the endothelial lid 4). Furthermore, the advantage of having a transparent bioreactor allows cutting the graft with a LASER advantageously at any moment during the bank storage stage 2. This may be carried out either on the endothelial side or on the epithelial. It may be made easier by the flattening of the cornea by the epithelial lid 5.

The bioreactor may be used advantageously in either direction, however the usual position is with the corneal specimen oriented with the epithelium down. In this position, it is impossible for any air bubble present in the circuit to remain trapped under the corneal dome on the endothelial side. Conversely, these bubbles could actually perturb the observation of the cornea and the analysis of the corneal endothelium.

The bioreactor may also be used advantageously vertically for example to examine the cornea with the standard ophthalmologist slit lamp.

The examination of the corneal endothelium during storage stage 2 can advantageously made easier by flattening the corneal dome with the epithelial lid 5 removing the corneal curvature which makes focusing difficult and is a source of parallax error.

The technical orifices 7c and 11c can allow the injection of reagents required for performing a modification of the corneal specimen cells during storage stage 2 in order to carry out a cell therapy of the graft by cell transfection using viral, chemical or physico-chemical vectors for example.

These technical orifices allow removing samples of preservation medium samples to carry out microbiological sterility tests during stage 2.

During the operating theater transplant stage 3, the cornea specimen may be cut with a LASER directly in the bioreactor 1, if not performed at the cornea bank, with or without flattening the corneal dome with the epithelial lid 5.

The bioreactor 1 is open at the last possible moment during the operating theater transplant stage 3 prior to carrying out the transplantation. It is the only time the bioreactor is open. The additional locking means 14b are unlocked by the operating room nurse to allow the separation of the endothelial lid 4 and the intermediate component 2. The cornea specimen 3 thus remains lodged in the central cavity of the intermediate component 2 and the surgeon takes it using a sterile surgical clamp.

Referring to FIG. 7, the bioreactor 1, in assembled position, is an airtight assembly containing a cornea specimen 3 firmly entrapped between the intermediate component 2 and the endothelial lid 4. The orifices of the intermediate components and of the endothelial lid are connected via the preservation medium circulation and the creation of a pressure gradient with overpressure on the endothelial side.

The bioreactor 1 may be used and maintain its properties in any position. It can therefore be placed in front of any optical instrument: for example it can be positioned in front of an ophthalmologist slit lamp in the vertical position.

Figure 8:
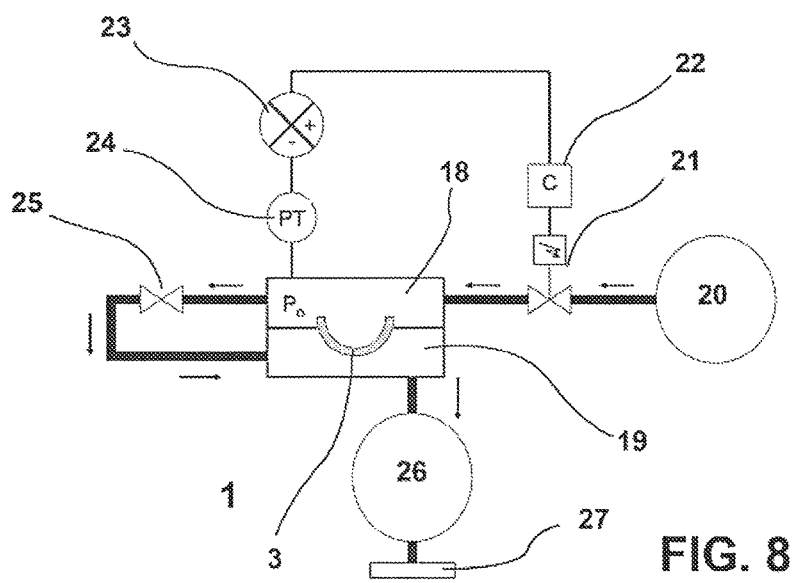
FIG. 8 is a flow diagram of the overpressure regulation system in the endothelial chamber using an electronic control mode.

Referring to FIG. 8, the bioreactor 1 is connected via tubes to the different elements that secure the circulation of the preservation medium in the two chambers (endothelial 18 and epithelial 19) and the maintenance of the pressure gradient with overpressure in the endothelial chamber. In FIG. 8 the pressure is regulated actively by an electronic device. The pressure Po in the endothelial chamber 18 is greater than that of the epithelial chamber 19. This Po pressure is adjustable but it could be the physiological intraocular pressure ranging from 12 to 20 mmHg. For instance, this pressure may be regulated as follows: in a production form the preservation medium is contained in a pressurized reservoir 20 (for example an elastomeric membrane, spring or pressurized gas infusion device), in another production form the preservation medium is injected by a pump. This reservoir enables the injection of liquid in the endothelial chamber 18 of the bioreactor. The injection is controlled (in duration and frequency) by a micro-solenoid valve 21 according to the pressure Po found in the endothelial chamber. This regulation is carried out by a control loop including a pressure transducer 24 which measures continuously or according to a pre-established Po frequency. The regulator 22 gives the solenoid valve opening or closing order according to a set point 23 determined by the operator (e.g., 12 to 20 mmHg). At the outlet of the endothelial chamber the preservation liquid goes through a second passive valve 25 which reduces the flow rate and prevents a sudden collapse of the Po when the solenoid valve is closed and no liquid is injected. This second valve could be a fine glass capillary flow restrictor or a passive valve that only open above a certain pressure (so-called check-valve). The preservation medium is then sent into the epithelial chamber 19 then in to a reservoir used as a "waste container" 26 and opened at atmospheric pressure through a filter 27 that prevents backflow microbiological contamination.

Figure 9:
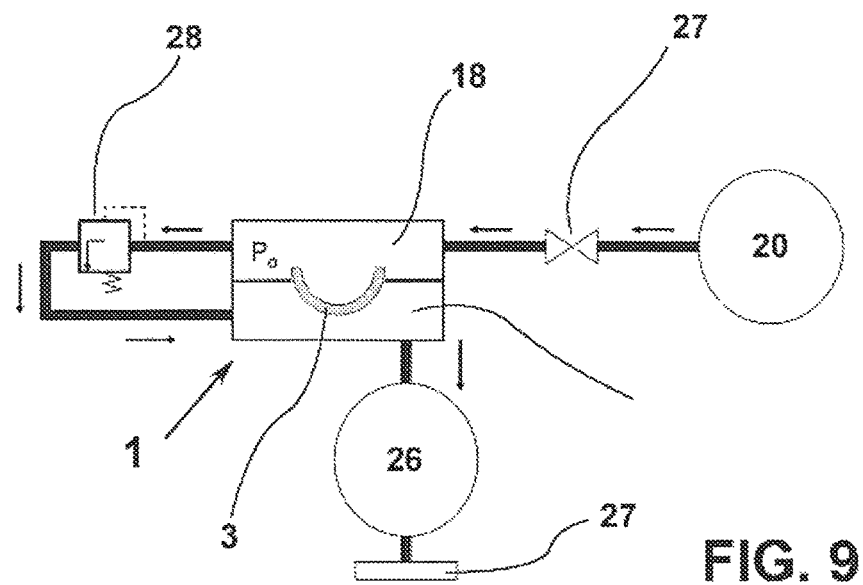
FIG. 9 is a flow diagram of the overpressure regulation system in the endothelial chamber using a passive control mode without electric input by passive control valve (check valve).

Referring to FIG. 9, the pressure gradient can also be regulated passively. The preservation medium is contained in a pressurized reservoir 20 for example an elastomeric membrane, spring or pressurized gas infusion device or by a pump. This reservoir enables the injection of liquid in the endothelial chamber 18 of the bioreactor 1. A flow regulator 27, for example a thin glass capillary, at the reservoir outlet 20 allows a slow and regular injection in the endothelial chamber 18. One or several control valves (called check-valve) 28 is placed at the outlet of the endothelial chamber

18 selected to open when Po attains the desired pressure (for example 12 to 20 mmHg). In this manner Po never exceeds the chosen pressure and is kept there as long as the medium is injected into the endothelial chamber 18. The preservation medium is then sent into the epithelial chamber then into a reservoir used as a waste container 26 and opened at atmospheric pressure through a filter 27 that prevents backflow microbiological contamination.

It goes without saying that the invention is not limited to the production form described above as an example but that it encompasses all forms of production covered by the claims attached.

The biological interest and flattening interest may be exposed as follows:

The device claimed comprises means 2, 4, 5. The device claimed allows keeping alive over several weeks under sterile conditions a human cornea for cornea transplantation in a patient and to keep alive over several weeks under sterile conditions a human or animal cornea for basic or pre-clinical research ex vivo laboratory experiments.

The adjustable pressure gradient between the endothelial side and the epithelial side with overpressure on the endothelial side limits the appearance of cornea stroma oedema, reduces it when it is present prior to placing the corneal specimen in the bioreactor, limiting the appearance of posterior corneal folds and improving the viability of the cornea cells, especially endothelial cells.

The corneal bioreactor may be used in any position, in particular horizontally or vertically.

When it is used in a horizontal position with the corneal epithelium pointed down any air bubble present in the circuit cannot accumulate under the corneal dome and do not perturb the examination of the cornea.

The transparent lid of the epithelial compartment can be displaced in an accurate and adjustable manner to come into contact with the corneal epithelium and flatten (iron out) the corneal dome by a flat (or curved) surface in order to facilitate the corneal sections using a LASER process.

This lid, which is made out of a transparent material compatible with the passage of ultrasounds, enables carrying out ultrasonography in order to be able to measure the thickness of the cornea before and/or after LASER cutting or by any other method without opening the bioreactor.

The epithelial lid may be removed while keeping the overpressure in the endothelial compartment 18. This may enable carrying out corneal sections by manual dissection or by microkeratome. This could be useful in ex vivo experiments where the instillation of substances is required on the epithelial side of the cornea exposed to the ambient air.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device for storage of a corneal specimen including a cornea and a sclera ciliary zone, comprising:
    an intermediate component including a first hole having a diameter matching that of the cornea, the first hole surrounded by a circumferential groove and a first edge, the first hole, groove, and first edge forming a cavity to receive the corneal specimen, the cavity configured to ensure that the corneal specimen is centered when inserted into the device and configured to stabilize the corneal specimen when the device is opened at an operating theater;
    an endothelial lid including a second hole having a diameter matching that of the cornea, the second hole surrounded by a second edge configured to trap the corneal specimen by flattening the sclera ciliary zone on the circumferential groove of the intermediate component; and
    an epithelial lid;
    wherein the intermediate component and the endothelial lid are configured to entrap the sclera ciliary zone in an airtight manner to delimit an endothelial chamber and an epithelial chamber separate from the endothelial chamber;
    wherein the endothelial chamber is composed of a space formed between the endothelial lid and the intermediate component after a tight connection of the endothelial lid to the intermediate component;
    wherein the epithelial chamber is composed of a space formed between the intermediate component and the epithelial lid after a tight connection of the epithelial lid to the intermediate component;
    wherein the intermediate component and the endothelial lid each comprise a respective inlet orifice and a respective outlet orifice, the orifices allowing a preservation medium to circulate through the endothelial chamber and through the epithelial chamber;
    the inlet orifice of the endothelial lid being connected to a preservation medium reservoir containing the preservation medium, such that during use the preservation medium contained in the preservation medium reservoir flows into the endothelial chamber from the preservation medium reservoir;
    the outlet orifice of the endothelial lid being connected to the inlet orifice of the intermediate component, such that during use the preservation medium contained in the endothelial chamber flows into the epithelial chamber from the endothelial chamber,
    the outlet orifice of the intermediate component being connected to a waste reservoir, such that during use the preservation medium contained in the epithelial chamber flows into the waste reservoir from the epithelial chamber,
    the connections of the orifices allowing the preservation medium to circulate on both sides of the cornea, firstly in the endothelial chamber and secondly in the epithelial chamber, and allowing the creation of a pressure gradient between the endothelial chamber and the epithelial chamber with overpressure in the endothelial chamber.

2. The device according to claim 1, wherein the endothelial lid comprises a notch that allows passing a microscope objective or any other instrument that needs to be close to the cornea for analysis or treatment of the cornea through the device.

3. The device according to claim 1, wherein the overpressure is equal to the physiological intra-ocular pressure.

4. The device according to claim 1, wherein the device is configured to generate and regulate the pressure gradient and the overpressure either passively using passive control valves opening at a desired pressure, or actively via feedback of a micro-solenoid valve controlling injection of the preservation medium into the endothelial chamber according to a set point set as a function of a pressure in the endothelial chamber measured by a pressure micro sensor.

5. The device according to claim 1, wherein the endothelial lid comprises a groove as a continuum with its inlet orifice allowing arrival of fresh preservation medium directly on corneal endothelium.

6. The device according to claim 1, wherein the endothelial and epithelial chambers each comprise a technical orifice that allows removal of preservation medium samples for microbiological or biochemical analysis purposes, or the injection of any substance, without compromising sterility within the device.

7. The device according to claim 1, wherein the endothelial and epithelial lids are transparent.

8. The device according to claim 1, wherein the device is configured to regulate a temperature of the preservation liquid within a range from 1 to 40 degrees Celsius.

9. The device according to claim 1, wherein the endothelial lid includes a first section comprising the second hole and a second section that is transparent.

10. The device according to claim 1, wherein the endothelial lid and the intermediate component include locking components for locking them to one another in an airtight manner.

11. The device according to claim 10, wherein the locking components include rails on the endothelial lid and a locking system comprising a slanted edge groove mounted on the rails so that when the locking system slides on the rails, the endothelial lid and the intermediate component are progressively tightened toward one another.

12. The device according to claim 11, wherein the locking components include micro crenations.

13. The device according to claim 1, wherein the epithelial lid and the intermediate component are assembled in an airtight manner.

14. The device according to claim 1, wherein the intermediate component extends between the endothelial lid and the epithelial lid when the device is assembled.

* * * * *